(12) United States Patent
Duan et al.

(10) Patent No.: US 9,999,415 B2
(45) Date of Patent: Jun. 19, 2018

(54) AUXILIARY APPARATUS FOR MINIMALLY INVASIVE SURGERY AND METHOD TO USE THE SAME

(71) Applicant: Ankon Medical Technologies (Shanghai), LTD., Shanghai (CN)

(72) Inventors: Xiaodong Duan, Pleasanton, CA (US); Shaobang Zhang, Hangzhou (CN)

(73) Assignee: Ankon Medical Technologies (Shanghai), LTD, Shanghai (CN)

( * ) Notice: Subject to any disclaimer, the term of this patent is extended or adjusted under 35 U.S.C. 154(b) by 292 days.

(21) Appl. No.: 14/875,738

(22) Filed: Oct. 6, 2015

(65) Prior Publication Data
US 2017/0035407 A1 Feb. 9, 2017

(30) Foreign Application Priority Data

Aug. 6, 2015 (CN) .......................... 2015 1 0477005

(51) Int. Cl.
*A61B 17/02* (2006.01)
*A61B 34/00* (2016.01)
*A61B 17/122* (2006.01)
*A61B 17/00* (2006.01)

(52) U.S. Cl.
CPC .......... *A61B 17/0218* (2013.01); *A61B 34/73* (2016.02); *A61B 17/122* (2013.01); *A61B 2017/00269* (2013.01); *A61B 2017/00477* (2013.01); *A61B 2017/00876* (2013.01)

(58) Field of Classification Search
CPC ... A61B 34/70; A61B 17/00234; A61B 34/30; A61B 2017/00269; A61B 17/0218; A61B 34/73; A61B 2017/00876; A61B 17/122; A61B 2017/00477
See application file for complete search history.

(56) References Cited

U.S. PATENT DOCUMENTS

| 5,337,472 A | * | 8/1994 | Leupold ................ H01F 7/0278 29/415 |
| 5,352,192 A | | 10/1994 | Byrne, et al. |
| 5,704,939 A | * | 1/1998 | Justin ................. A61B 17/7216 606/62 |
| 8,137,268 B2 | * | 3/2012 | Van Lue .................. A61B 1/24 600/12 |

(Continued)

FOREIGN PATENT DOCUMENTS

| CN | 102247179 | 11/2011 |
| WO | 2009023136 | 2/2009 |

(Continued)

*Primary Examiner* — Zade Coley
(74) *Attorney, Agent, or Firm* — Treasure IP Group, LLC

(57) ABSTRACT

An auxiliary apparatus for MIS including an in vivo device and an in vitro device to stretch a surgery target is provided. The in vitro device comprises an in vitro magnet field-generating element. The in vivo device comprises an in vivo magnet-anchoring element to the surgery target. The in vivo magnet moves and/or rotates according to the direction change of the external magnetic field, which is generated by the in vitro magnet field-generating element, and thereby the surgery target can move in a controlled speed and/or rotate in a controlled angle according to the direction change of the external magnetic field. A method to control the auxiliary apparatus is also provided.

3 Claims, 29 Drawing Sheets

(56) References Cited

U.S. PATENT DOCUMENTS

| | | | |
|---|---|---|---|
| 8,623,011 B2 | 1/2014 | Spivey | |
| 8,701,677 B2* | 4/2014 | Duan | A61B 1/00158 128/898 |
| 8,764,769 B1 | 7/2014 | Rodriguez-Navarro, et al. | |
| 8,790,245 B2* | 7/2014 | Rodriguez Fernandez | A61B 17/3421 600/106 |
| 8,827,891 B2 | 9/2014 | Roberts | |
| 8,852,088 B2 | 10/2014 | Ransden, et al. | |
| 2006/0015002 A1* | 1/2006 | Moaddeb | A61B 17/00234 600/37 |
| 2007/0135678 A1* | 6/2007 | Suzuki | A61B 17/0401 600/37 |
| 2009/0043246 A1* | 2/2009 | Dominguez | A61B 17/0218 604/21 |
| 2010/0049204 A1* | 2/2010 | Soubeiran | A61B 17/025 606/90 |
| 2010/0228167 A1* | 9/2010 | Ilovich | A61B 17/7216 601/89 |
| 2011/0295067 A1* | 12/2011 | Rodriguez Fernandez | A61B 17/3421 600/114 |
| 2011/0295285 A1* | 12/2011 | McWeeney | A61B 17/1114 606/153 |
| 2012/0165825 A1* | 6/2012 | Theophilopoulos | A61B 17/083 606/118 |
| 2013/0085341 A1 | 4/2013 | Nobis | |
| 2013/0267788 A1* | 10/2013 | Duan | B25J 11/00 600/300 |
| 2013/0289581 A1 | 10/2013 | Yeung et al. | |
| 2014/0247039 A1* | 9/2014 | Duan | B25J 11/00 324/207.11 |
| 2014/0273084 A1* | 9/2014 | Boehl | G01N 1/31 435/40.52 |

FOREIGN PATENT DOCUMENTS

| | | |
|---|---|---|
| WO | 2011044468 | 4/2011 |
| WO | 2013096470 | 6/2013 |

* cited by examiner 2901 target organ
2903 target lesion area to be removed
2905 a previous position of the target lesion area
2907 cutting line
2908 overall progressive movement direction of the target lesion area
2909 rolling up of the separated portion of the target lesion area

AUXILIARY APPARATUS FOR MINIMALLY INVASIVE SURGERY AND METHOD TO USE THE SAME

BACKGROUND

1. Technical Field

The present disclosure relates to an auxiliary apparatus for minimally invasive surgery, and, more particularly, for assisting pulling or cutting off a target lesion area in a surgery.

2. Description of Related Art

Minimally invasive surgery (MIS) utilizes medical scopes, such as gastroscope, enteroscopy, laparoscopy, thoracoscope and relative tools to perform a surgery. The concept of minimal invasion derives from the development of the whole medical pattern and the idea of entire treatment. MIS focuses on the progress and recovery of patients' psychology, sociality, physical pain, spirit and life quality. It takes care of patients and reduces their suffering. During an MIS procedure, surgery targets are accessed through natural orifices or from one to three small incisions 0.5 cm to 1 cm in length, rather than through a large incision in an open surgery approach. The advantages of MIS over conventional surgeries include minimal scar, decreased pain, less hospital time and quick recovery. Therefore, MIS reduces damages and brings convenience to patients.

Endoscopic Submucosal Dissection (ESD), a type of MIS, is applied in early carcinoma or pre-carcinoma abnormalities. More particularly, ESD adapts to patients with mucosal or submucosal invasion and without regional lymph node or distant metastasis. In clinic, ESD is usually used in the following diseases in a digestive tract: (1) polyps and pre-carcinoma abnormalities, especially with surgery targets >2 cm in diameter, in which ESD can completely remove abnormal tissues; (2) early cancer, especially limited to mucosa without lymph node metastasis, may be cured by ESD coupled with chromo endoscopy and ultrasonic endoscopy, which can be as effective as conventional surgery; (3) submucosal cancer, such as leiomyoma, stromal tumor, lipoma and tumors originated from mucosa and submucosa, in which ESD can dissect abnormal tissues. In Japan, almost over half of early stomach cancers and colon cancers are treated with ESD at present.

ESD expands indications for the resections with endoscopy. Early cancer and pre-cancer abnormality in the gastrointestinal tract can be treated effectively due to the thorough removal of abnormal tissues by ESD. Compared with conventional surgery, ESD has less trauma and is more endurable for patients. It is possible to design a personal strategy according to the site, size, shape and features of the abnormal tissues so as to retain normal tissues and functions while a tumor is completely removed. However, during the operation of ESD, the visualization of the surgical field is narrowed because the surgery target on the resected mucosa moves down for gravity, which affects the performance of ESD.

SUMMARY OF INVENTION

The present disclosure aims at the disadvantages of the previous art to provide an auxiliary apparatus for MIS and a method to control it to enlarge the visual field of surgery.

The present disclosure provides an auxiliary apparatus for MIS, including an in vivo device and an in vitro device, to maneuver a surgery target. The in vitro device comprises an in vitro magnetic field generating element. The in vivo device includes an in vivo magnet anchoring element for the surgery target. The in vivo magnet can move and/or rotate according to the direction change of the external magnetic field, which is induced by the in vitro magnetic field generating element, and thereby the surgery target moves in a controlled speed and/or rotates in a controlled angle according to the direction change of the external magnetic field.

In one embodiment, the in vitro magnetic field generating element provides a uniform magnetic field.

In another embodiment, the in vitro magnetic field generating element is a spherical magnet or Helmholtz coil.

In another embodiment, the in vitro device comprises robotic arms, and a spherical magnet, which is controlled by robotic arms to move and/or rotate in three dimensions.

In another embodiment, the in vivo device is further comprised of one or more magnetic cylinders, connected side by side, and each has a column shaped hollow center, a length of about 2 mm to 20 mm, an external diameter of about 1.5 mm to 10 mm, and an internal diameter from 0.3 mm to 2.4 mm.

In another embodiment, the length of the magnetic cylinder is from 2 mm to 3 mm with the external diameter from 1.5 mm to 2.5 mm and the internal diameter from 0.3 mm to 1.4 mm.

In another embodiment, the magnetic cylinder having a column shaped hollow center is longitudinally polarized.

In another embodiment, the in vivo magnet is comprised of odd numbered magnetic cylinders, which are radially polarized and connected to each other side by side.

In another embodiment, the in vivo device further comprises a clip to anchor the in vivo device to the surgery target and a connector to join the clip with the in vivo magnet.

In another embodiment, the in vivo device comprises two clips to anchor the in vivo device to the surgery target and a connector, which joins the two clips to each side of the in vivo magnet respectively.

In another embodiment, the in vivo device comprises a clip to anchor the in vivo device to the surgery target, and the clip is jointed to a side of the in vivo magnet.

In another embodiment, the in vivo device comprises two sets of in vivo magnets, which are spaced apart, and a stiff connector to join the two sets of in vivo magnets, and the clip can take hold of the stiff connector.

In another embodiment, a loop is formed at an end of the connector by a tying scaffold, midshipman's hitch or a slip knot, and the loop may encircle the clip and join the clip to the connector by pulling to reduce the diameter of the loop.

In another embodiment, the in vivo device comprises a holding set which houses a portion of the connector to enable the clip to take hold of the connector and in which the holding set comprises plastic tubes or silicone tubes.

In another embodiment, the clip is made of pure titanium or medical grade alloy.

In another embodiment, the in vivo magnet is made of NdFeB, $Fe_3O_4$, SmCo or AlNiCo.

In another embodiment, the in vivo magnet is plated with a biocompatible film of titanium, nickel or fluoride.

In another embodiment, the in vitro spherical magnet is a permanent magnet, made of NdFeB, $Fe_3O_4$, SmCo or AlNiCo.

In another embodiment, the in vivo device comprises a supporting set to integrate the in vivo magnet into an assembly; the supporting set comprises a base and a top cover; the base comprises a bed to attach with the top cover and limit the in vivo magnet from moving along a length direction of the supporting set, and a supporting column which runs from the bed to the top cover to limit the in vivo magnet to move along a radial direction of the supporting set; the top cover comprises a cavity to receive and fasten a distal end of the supporting column, which is distant from the bed; and a hole is disposed between the base and the top cover for the connector to pass along the length direction of the supporting set.

The present disclosure provides a method for the controlling of the auxiliary apparatus. The method comprises the steps of: a) starting the in vitro magnetic field generating element to provide a magnetic field interacting with the in vivo magnet; b) controlling the change of direction of the magnetic field to manipulate the in vivo magnet which in turn makes the surgery target wrap the in vivo magnet.

In an embodiment, the in vitro magnetic field generating element provides a uniform magnetic field.

The advantages of the present disclosure include: the auxiliary apparatus induces rotatable a magnetic field via in vitro magnetic field generating element. The in vivo magnet can move and/or rotate in accordance with a direction change of an external magnetic field which is generated by the in vitro magnetic field generating element, and thereby the surgery target can move in a controlled speed and/or rotate in a controlled angle in accordance with the direction change of the said external magnetic field. Therefor, the resected surgery target can overcome gravity to expose the visual field for dissection and improve the efficiency of resection. Moreover, the method to control the disclosed auxiliary apparatus makes the surgery target cling to the in vivo device via the magnetic field created by the in vitro magnetic field generating element to expand the visual field.

The foregoing has outlined rather broadly the features and technical advantages of the present disclosure in order that the detailed description of the invention that follows may be better understood. Additional features and advantages of the invention will be described herein after which form the subject of the claims of the invention.

BRIEF DESCRIPTION OF THE DRAWINGS

The components in the drawing are not necessarily drawn to scale, the emphasis instead being placed upon clearly illustrating the principles of the described embodiments. In the drawings, reference numerals designate corresponding parts throughout various views, and all the views are schematic.

DETAILED DESCRIPTION OF ILLUSTRATED EMBODIMENTS

Figure 1:
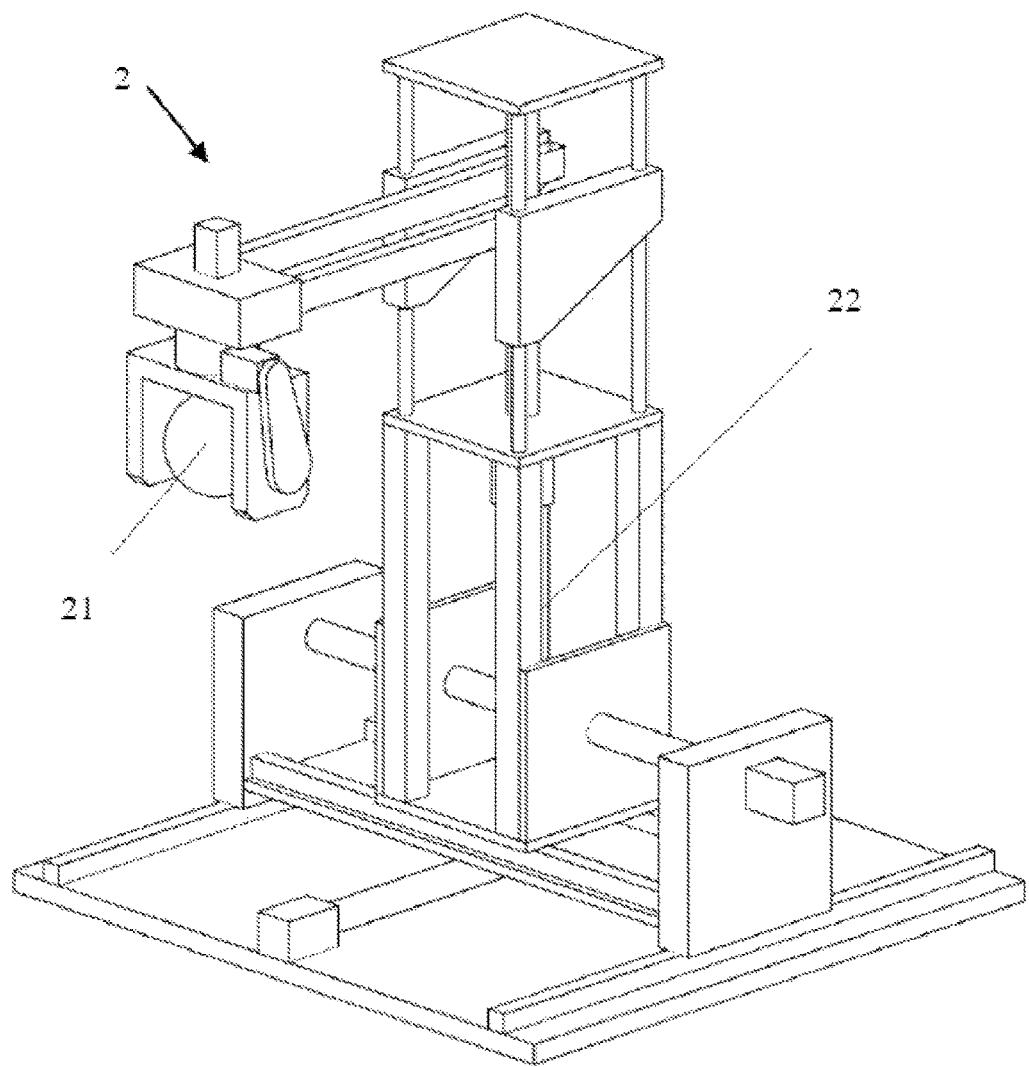
FIG. 1 depicts an in vitro device in accordance with the present disclosure.
Figure 2:
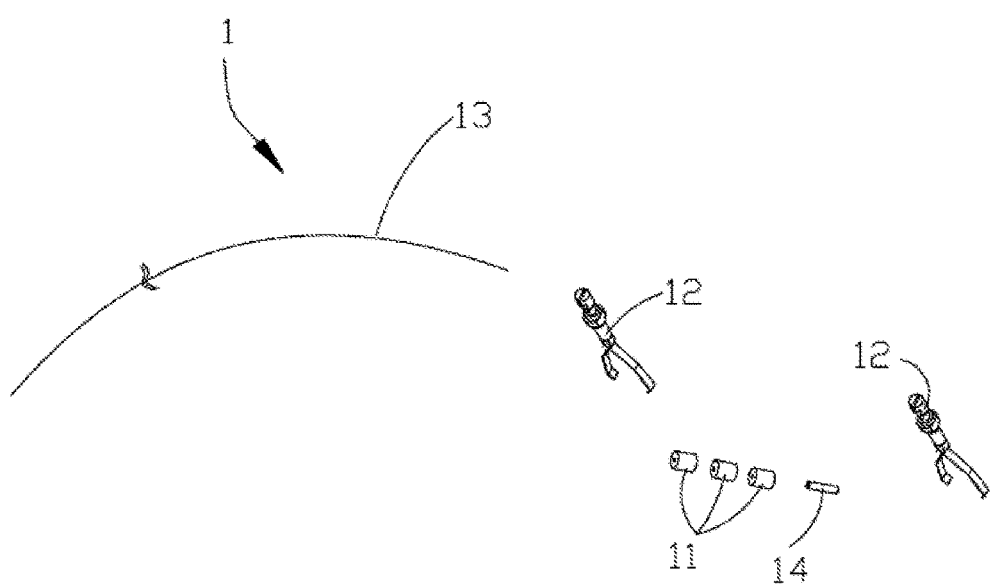
FIG. 2 depicts an in vivo device in accordance with the first embodiment of the present disclosure.

Reference will now be made to the drawing figures to describe the embodiments of the present disclosure in detail. In the following description, the same drawing reference numerals are used for the same elements in different drawings.

FIG. 1 to FIG. 25 schematically depict that the disclosed auxiliary apparatus (unlabeled), which is adapted to MIS such as ESD and endoscopic mucosal resection (EMR), results in enlargement of the visual field of a surgery via stretching the surgery target 3. In details, the operator makes an incision on the mucous membrane at an end of the surgery target 3. The said auxiliary apparatus is then anchored on the resected mucous membrane and stretches the surgery target 3 to separate it from the mucous membrane or muscles, causing enlargement of the visual field and improvement of performance.

The said auxiliary apparatus for MIS includes an in vivo device 1 which is mounted inside the body cavity, in use, to fix a surgery target, and an in vitro device 2 to control the mobility of the in vivo device 1. The in vivo device 1 takes hold of the surgery target 3, followed with moving or rolling driven by the in vitro device 2, and results in the resected or dissected surgery target 3 to overcome gravity, causing exposure of the visual field in surgery.

Most endoscopies are made of magnetically soft steel. It is significant for the application of the present disclosure that the in vitro device 2 functions as an in vivo magnet 11 with limited effect on the ferromagnetic material endoscope. Magnetic force is typically hard to eliminate in the foregoing effect. The in vivo magnet 11 is adjacent to the endoscope. Usually, if the magnetic force on an endoscope is weak, it is the same on the in vivo magnet 11.

The in vitro device 2 includes a magnetic field generating element outside the body, which provides a rotatable magnetic field. The in vivo device 1 includes an in vivo magnet 11 which may anchor to the surgery target 3. The in vivo magnet 11 is able to move and/or rotate due to the direction change of the external magnetic field, which is induced by the magnetic field generating element outside the body. Accordingly, the surgery target 3 moves in a controlled speed and/or rotates in a controlled angle to wrap the in vivo device 1.

In a preferred embodiment, the in vitro device 2 includes a magnetic field generating element outside the body, which provides a uniform magnetic field. The uniform magnetic field can be a uniform magnetic field, approximate uniform magnetic field, and uniform magnetic field in a portion of the space. Therefore, the in vitro device 2 may provide a uniform magnetic field interacting with the in vivo device 1. The rotating uniform magnetic field can be utilized in this instance. The magnetic field generating element outside the body utilizes a spherical magnet 21 or Helmholtz coil to generate the rotating uniform magnetic field in a random direction.

If the magnetic field is uniform, according to the formula $\vec{F}=\vec{m}\cdot\nabla\vec{B}=0$, the magnetic force is zero;

But the magnetic force is short lasting according to the formula $\vec{T}=\vec{m}\times\vec{B}=m\cdot B\cdot\sin\theta$. Herein, "$\theta$" is the angle between the permanent magnet and the magnetic field outside the body. The soft magnetic materials are magnetized in the magnetic field. When the magnetic field is removed, magnet torque (m) is back to zero.

$\vec{m}=\mu\cdot\vec{B}\cdot a$. Herein, "$\mu$" is magnetoconductivity. "B" is external field. "a" is a factor for shape. For a sphere, the factor "a" doesn't change with angle. For other shapes, the factor "a" is variable according to angle.

If the magnetic field is uniform, according to the formula $\vec{T}=\vec{m}\times\vec{B}\approx\mu a\,\vec{B}\times\vec{B}=0$, the magnet torque interacting with soft magnetic materials is zero.

Therefore, the uniform external magnetic field may drive the in vivo magnet 11 to move and/or rotate via the magnet torque. Accordingly, the resected or dissected surgery target 3 overcomes gravity and gets curling to wrap the in vivo device 1 to expose the visual field for resection without effect to the endoscope.

For an example of a Helmholtz coil, three pairs of Helmholtz coils are placed vertically. Each pair of Helmholtz coils is exerted with the same current to generate a relatively uniform magnetic field in the center. Herein, the diameters of Helmholtz coils in three dimensions are from 300 mm to 1000 mm, with the same coil constant. Adapted to the uniform magnetic field in three dimensions, the field intensity is from 10 Gs to 2000 Gs.

$$B = \frac{32\pi NI}{5\sqrt{5}a} * 10^{-7}$$

Herein, "N" is the number of coils. "I" is current (unit: A). "B" is field intensity (unit: T). "a" is radius (unit: m). The distance of each pair of coils is equal to its radius.

Three pairs of coils provide the magnetic fields in three directions $B_x$, $B_y$, $B_z$, $\hat{\mu}(\theta, \varphi)$. The general field intensity is B.

$B_x=B\cdot(\sin\varphi\cdot\cos(w\cdot t)-\cos\theta\cdot\cos\varphi\cdot\sin(w\cdot t))$
$B_y=B\cdot(-\cos\varphi\cdot\cos(w\cdot t)-\cos\theta\cdot\sin\varphi\cdot\sin(w\cdot t))$
$B_z=B\cdot\sin\theta\cdot\sin(w\cdot t))$ The magnetic field B rotates at angular velocity w on the surface with $\hat{\mu}(\theta, \varphi)$ in the normal direction. The torque exerted by the magnetic field B may drive the rotation of the in vivo magnet 11, which is fixed, on the surface of the abnormal mucosa to uncover. Since the direction of rotation is able to change randomly, $\theta$ and $\varphi$, the direction angle of $\vec{\mu}$, is also the functions of time $\theta(t)$, $\varphi(t)$. The direction to uncover the mucosa is able to be adjusted through $\theta(t)$ and $\varphi(t)$.

Moreover, the spherical magnet, which has the best uniformity among all shapes of permanent magnets, may be used to provide the uniform rotatable magnetic field. The spherical magnet has a dipole magnetic field with some certain of gradient magnetic field, which is called nonuniform.

$$\nabla B = \frac{\mu_0}{4\pi}\frac{6M}{r^4}, B = \frac{\mu_0}{4\pi}\frac{2M}{r^3}, r = \left(\frac{u_0 2M}{4\pi B}\right)^{1/3};$$

$$\nabla B / B = 3/r$$

$$\nabla B = 3B/r = 3B^{4/3}\left/\left(\frac{\mu_0 M}{2\pi}\right)^{1/3}\right.$$

If B is set, the bigger M is, the smaller $\nabla B$ is. M is proportional to the volume of the spherical magnet, therefore $\nabla B \propto (1/R)$. Herein, "R" is the radius of the spherical magnet.

The magnetic field performs better in uniformity for a spherical magnet with longer radius. Thereby, when the magnetic field is the same, the magnetic field of a big spherical magnet is better in uniformity than that of a small one.

Figure 23:
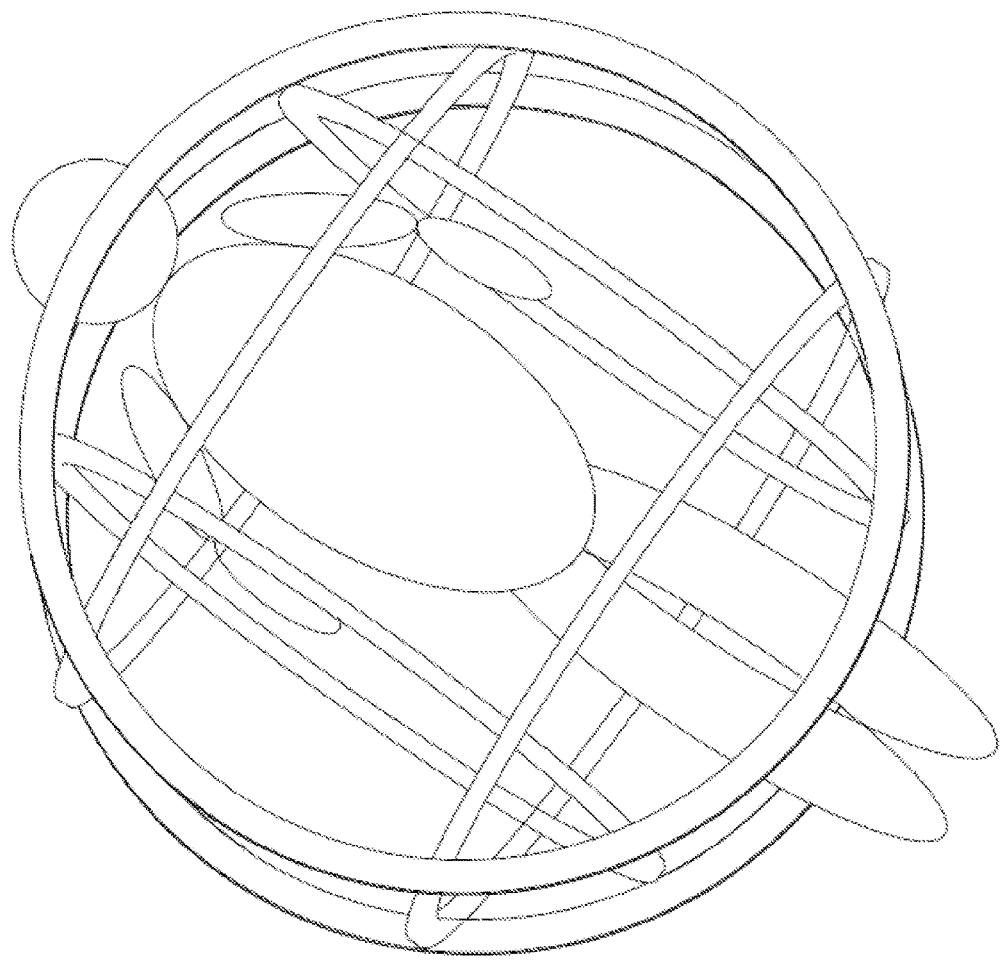
FIG. 23 depicts Helmholtz coil presenting a uniform magnetic field.

The uniform magnetic field generated by a Helmholtz coil is very similar to that of the spherical magnet with the exception of the methods controlling the in vivo magnet 11. FIG. 23 schematically depicts the uniform magnetic field provided by the Helmholtz coil.

A spherical magnet 21 will be used as an example to further explain the control of the in vivo magnet 11 by a magnetic field generating element outside the body. Referring to FIG. 1, the in vitro device 2 includes a spherical magnet 21, which is a permanent magnet or electrical magnet. In a preferred embodiment, the permanent magnet uses materials such as NdFeB, $Fe_3O_4$, SmCo or AlNiCo, which have little radiation hazard to the human body. The spherical magnet 21 can move and/or rotate in three dimensions outside the body to induce consequential movement and/or rotation of the in vivo magnet. More particularly, the spherical magnet 21 may move and rotate through the control of a human or machinery.

The in vitro device 2 includes a motor (not shown), a plurality of three-axis robot arms 22 driven by the motor, and a spherical magnet 21 controlled by the robot arms 22 to move and/or rotate in three dimensions outside the body. The three-axis robot arms 22 can be any machinery that may hold the spherical magnet 21 and drive it to move and/or rotate in three dimensions outside body. Structure for the robot arm 22 is not limited to this embodiment. The details about how the in vitro device 2 controls the spherical magnet 21 to move and/or rotate in three dimensions refer to the Chinese patent CN201310136094.0.

The spherical magnet 21 is constructed of various materials, including for example, NdFeB, $Fe_3O_4$, SmCo or AlNiCo. The dissected mucous membrane may overcome gravity to expose visual field during a MIS procedure through the change of distance between the spherical magnet 21 and the in vivo magnet 11 as well as the movement and/or rotation of the spherical magnet 21. Accordingly, the efficiency and accuracy of resection is improved.

The in vivo device 1 includes an in vivo magnet 11 matching with the spherical magnet 21, at least a clip 12 for the fixation of the in vivo device 1 and the surgery target 3, a connector 13 joining the clip 12 with the in vivo magnet 11, at least a holding set 14 housing a portion of the connector 13 for the grip of the clip 12, and a supporting set 15 integrating the in vivo magnet 11 into an assembly.

The clip 12 is made of medical grade titanium and is used to take hold of the surgery target 3. The medical grade titanium can be pure titanium or an alloy. The in vivo magnet 11 is a permanent magnet made of NdFeB, $Fe_3O_4$, SmCo or AlNiCo. The surface of the in vivo magnet 11 is plated with biocompatible film, which can be titanium, nickel or fluoride. In a preferred embodiment, the fluoride is polytetrafluoroethylene (PTFE).

Figure 26:
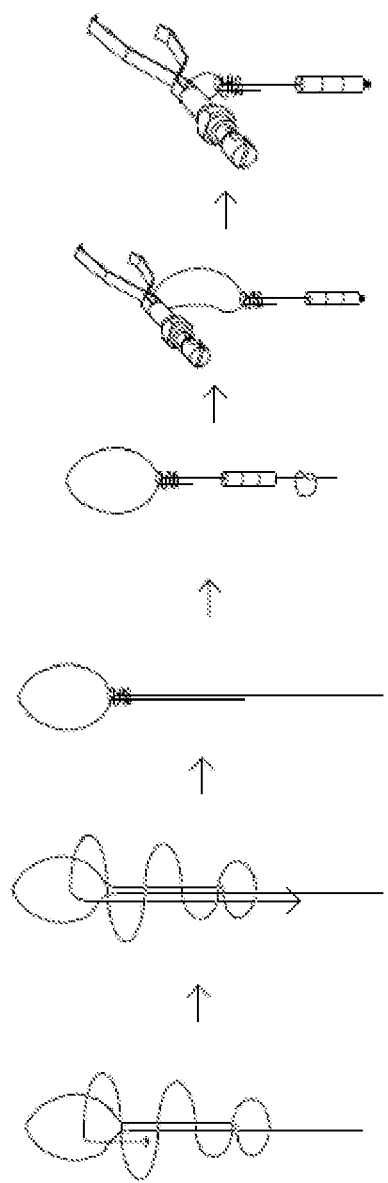
FIG. 26 depicts the steps by which a connector forms a loop by tying scaffold knot and joins to a clip.
Figure 27:
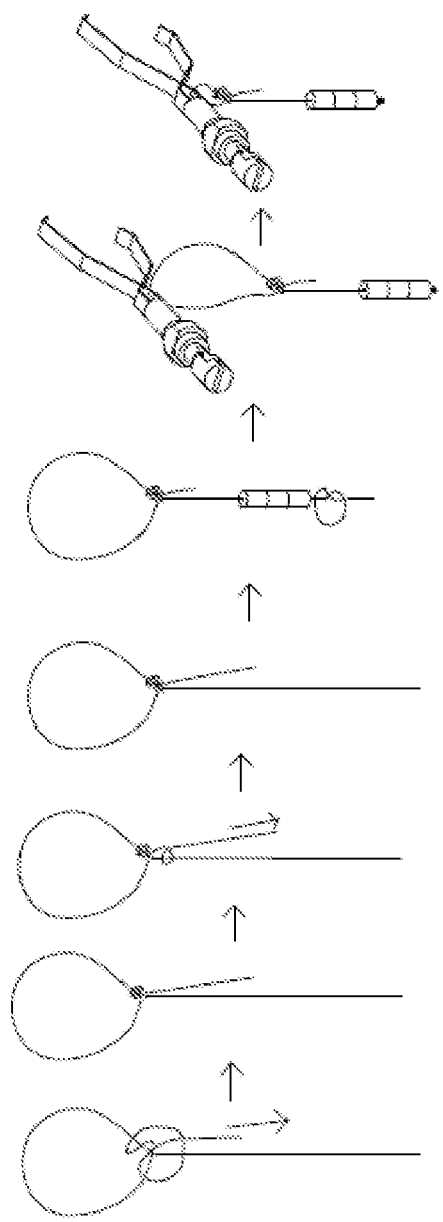
FIG. 27 depicts the steps by which a connector forms a loop by tying a midshipman's hitch and joins to a clip.
Figure 28:
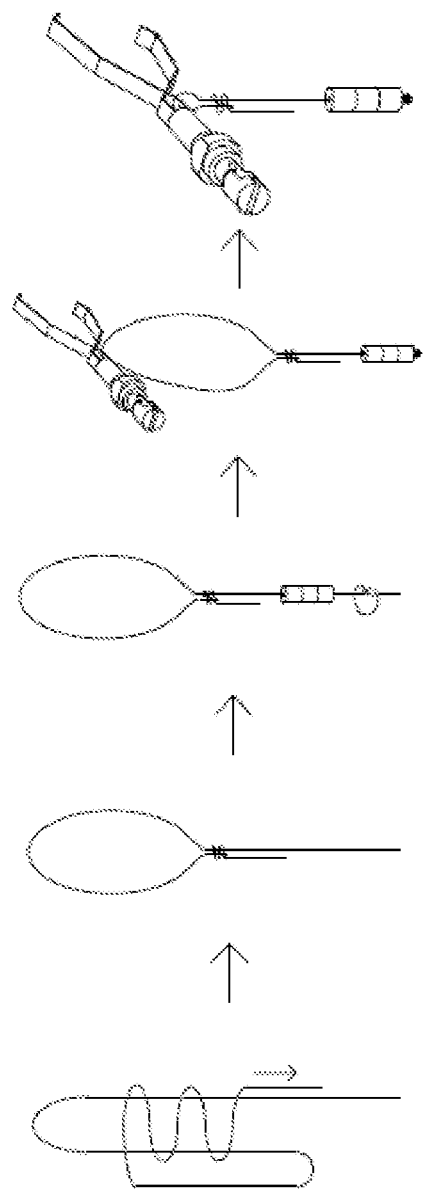
FIG. 28 depicts the steps by which a connector forms a loop by tying a slip knot and joints to a clip.

It is difficult to join the clip 12 to the connector 13 because the clip 12 is small in volume. As depicted in FIGS. 26, 27 and 28, an end of the connector 13 comprises a loop made in the manner of a scaffold, midshipman's hitch or slip knot. The loop includes a drawing member that may adjust the diameter of the loop. The loop encircles the clip 12, in use, and then is collapsed by pulling the drawing member to join the clip 12 to the connector 13. It is understandable that the joint means can be any means that would adapt to the linkage of the clip 12 and connector 13, and are not limited to the illustrations in FIG. 26-FIG. 28.

The connector 13 can be a soft or rigid connective thread. The holding set 14 is a tube, which is longer in diameter than the connective thread and made of soft plastic or silicone. The clip 12 grips the surgery target 3 and the holding set 14, in use, resulting in the stable fixation of the surgery target 3 and the in vivo device 1.

The in vivo magnet 11 is made of one or more magnetic cylinders each having a hollow column-shaped center. Stung by the connector 13, the magnetic cylinders are connected side by side via magnetic power. The self-arrangement of the magnetic cylinders inside the body forms the in vivo magnet 11 and thus reduces the requirement for the diameter of the orifices. In an embodiment, the length of each magnetic cylinder is from 2 mm to 3 mm with the external diameter from 1.5 mm to 2.5 mm and the internal diameter from 0.3 mm to 1.4 mm. The number of magnetic cylinders is determined by the size of the surgery target 3. The bigger the surgery target 3, the more the magnetic cylinders, and vice versa.

Figure 24:
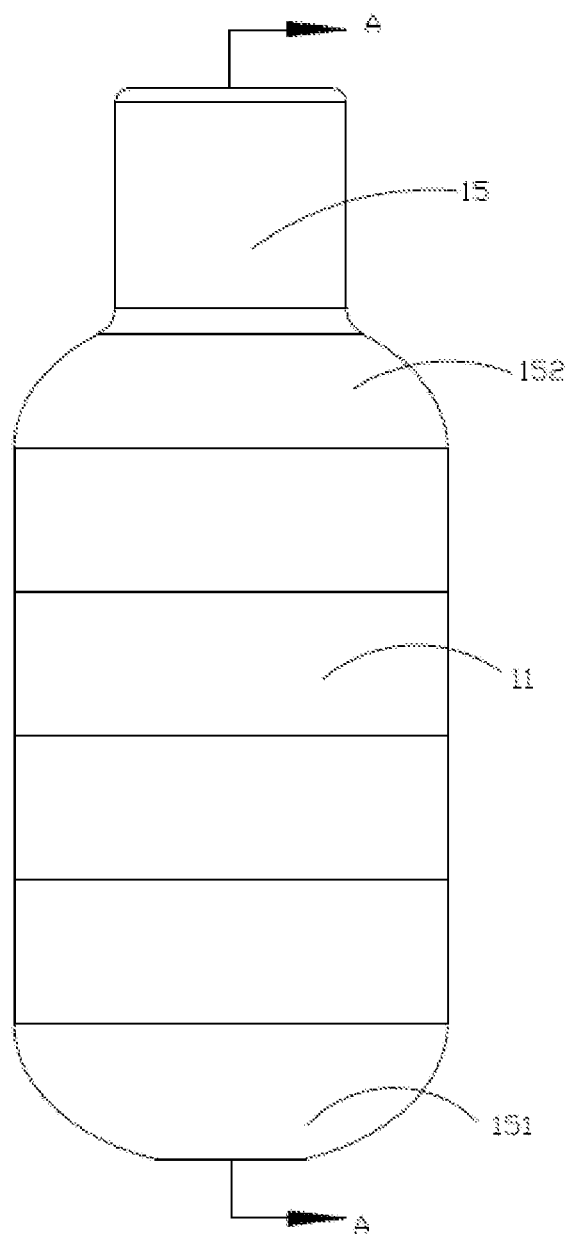
FIG. 24 depicts in vivo magnets which are integrated to an assembly by a supporting set.
Figure 25:
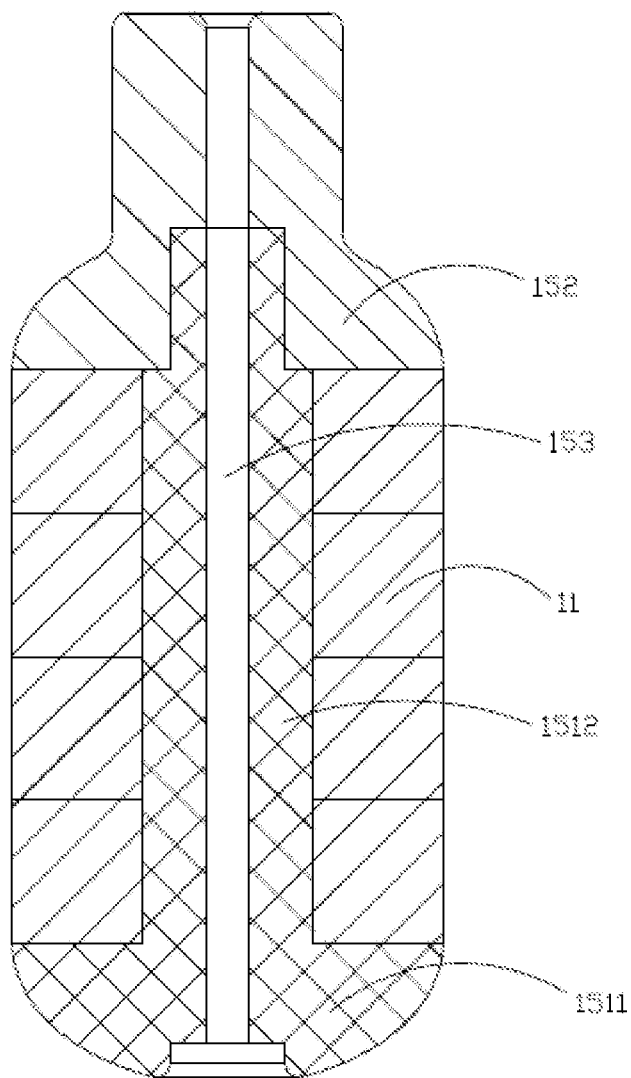
FIG. 25 depicts a section view of FIG. 24 along the A-A direction.

FIGS. 24 and 25 schematically illustrate the supporting set 15, in the shape of a column, which includes a base 151 and a top cover 152 which are made of PC. The base 151 comprises a bed 1511 and a supporting column 1512. The bed 1511 matches with the top cover 152 to limit the in vivo magnet 11 moving along the length direction of the supporting set 15. The supporting column 1512 runs from the bed 1511 to the top cover 152 to limit the in vivo magnet 11 moving along the radial direction of the supporting set 15.

The fixing end (unlabeled) is disposed at the distal end of the supporting column 1512, which is distant from the bed 1511. The diameter of the fixing end is shorter than that of the supporting column 1512. The diameter of the supporting column 1512 is shorter than that of the bed 1511. The top cover 152 comprises a cavity (unlabeled) to receive and fasten the fixing end of the supporting column 1512. A hole 153 is disposed between the base 151 and the top cover 152 for the connector 13 to pass along the length direction of the supporting set 15. The connective thread passes through the hole 153 to further engage with the clip 12 to be integrated.

The base 151 and the top cover 152 are uncovered, in use, and the supporting column 1512 is housed by the magnetic cylinders having hollow column-shaped centers. And then, the top cover 152 engages to the distal end of the supporting column 1512, which is distant from the bed 1511. Thereby, the in vivo magnet 11 is integrated by the supporting set 15. After that, the connective thread passes through the hole 153 to engage with the clip 12 to form an assembly.

One of the advantages using the supporting set 15 is to enlarge the internal diameter of the magnetic cylinders having hollow column-shaped centers while the diameter of the connective thread is fixed, which facilitates the internal coating of the magnetic cylinders having hollow column-shaped centers. If a plurality of magnetic cylinders having hollow column-shaped centers is applied, the cylinders are held by the base 151 and the top cover 152 to prevent them from falling apart.

In an embodiment, the in vivo device 1 includes two clips 12 fastening the in vivo device 1 and the surgery target 3, a connector 13 guiding the clips 12 to either side of the in vivo magnet 11 respectively and attaching the clips 12 to a side of the in vivo magnet 11. Herein, the tubes are made of soft plastic or silicone and are disposed at a side of the in vivo magnet 11.

The column-shaped magnetic cylinders are longitudinally polarized, and the polarization directions for all cylinders are identical. Optionally, the magnetic cylinders having hollow column-shaped centers can be radially polarized. In this instance, odd numbered, column-shaped magnetic cylinders, strung by the connective thread, are connected to each other side by side via the magnetic power to form the in vivo magnet 11. The adjacent magnetic cylinders are opposite in polarization direction.

FIG. 1 to FIG. 13 illustrates preferable embodiments. The auxiliary apparatus for MIS includes an in vivo device 1 and an in vitro device 2. The in vivo device 1 comprises hollow in vivo magnets 11, two clips 12, a connective thread and a holding set 14.

Figure 3:
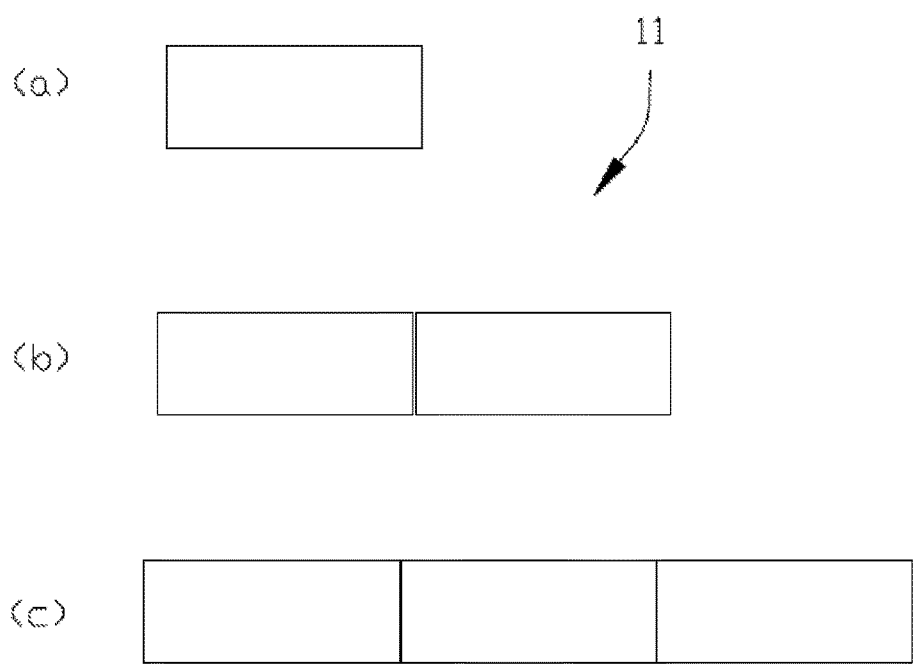
FIG. 3 depicts an in vivo magnet having magnetic cylinders in accordance with the present disclosure.

Referring to FIG. 3, an arbitrary number of magnetic cylinders having hollow column-shaped centers with about 2.5 mm in length and about 2 mm in diameter, strung by the connective thread, are connected to each other side by side through the magnetic power to form the in vivo magnets 11. Two clips 12 connect to either side of the in vivo magnet 11 through the connective thread. More specifically, FIG. 3 illustrates the length of the in vivo magnet 11 which is adjustable in accordance with the size of the surgery target 3 during an ESD procedure. In the case that the surgery target 3 is small, the in vivo magnet 11 is made of one magnetic cylinder having hollow column-shaped centers (depicted in a). If the surgery target 3 is medium, the in vivo magnet 11 is made of two magnetic cylinders connected side by side (depicted in b). If the surgery target 3 is large, the in vivo magnet 11 is made of three or more magnetic cylinders (depicted in c). The number of magnetic cylinders is adjustable in accordance with the size of the surgery target 3 instead of being restricted to set number.

Figure 4:
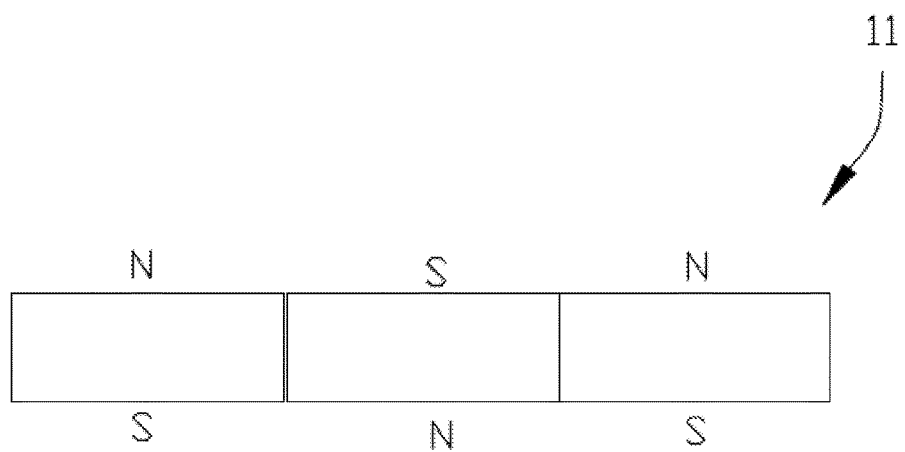
FIG. 4 depicts magnetic cylinders having column shaped hollow centers which are radially polarized in accordance with the present disclosure.
Figure 5:
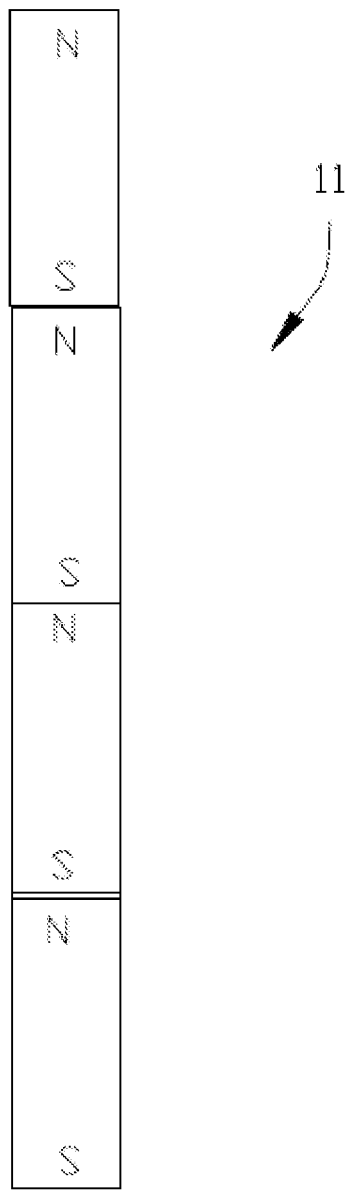
FIG. 5 depicts magnetic cylinders which are longitudinally polarized in accordance with the present disclosure.

FIG. 4 illustrates that the in vivo magnet 11 consists of odd numbered magnetic cylinders when the magnetic cylinders having hollow column shaped hollow centers are uniformly radially polarized. The adjacent magnetic cylinders are opposite in polarization direction. FIG. 5 illustrates that magnetic cylinders having hollow column-shaped centers are uniformly longitudinally polarized.

The magnetic cylinders are plated with a biocompatible film, which uses materials such as titanium, nickel or fluoride. The clip 12 is made of pure titanium or titanium alloy. Preferably, the number of the clips 12 is two. Two clips 12 and the in vivo magnet 11 are jointed by the connective thread when they are in use.

Figure 6:
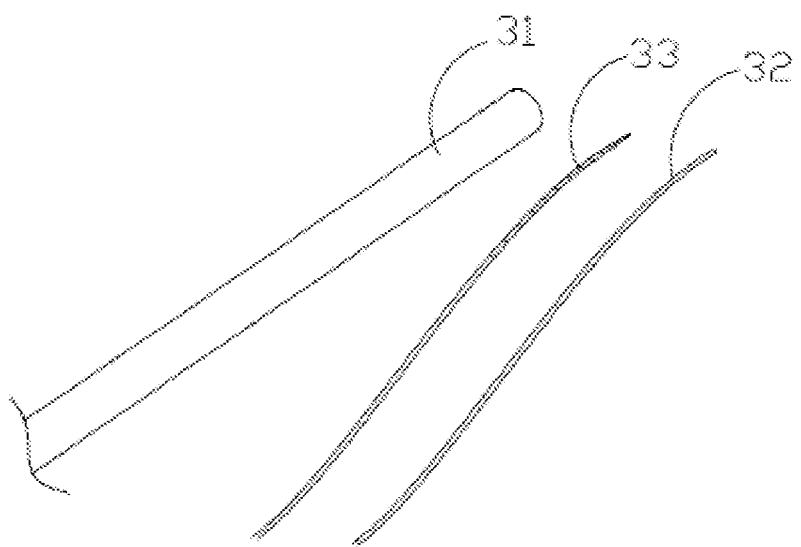
FIG. 6 depicts auxiliary tools used to facilitate the auxiliary apparatus for MIS.

FIG. 6 schematically illustrates some auxiliary tools applied in MIS which include a cannula-assisted endoscope 31, a guide wire 32 and a titanium clip releaser 33. The cannula-assisted endoscope 31 delivers the in vivo device 1, such as the in vivo magnet 11, the clip 12, the connective thread and the holding set 14, into the body cavity. The guide wire 32 facilitates the cannula-assisted endoscope 31 to deliver the in vivo magnet 11 and holding set 14. The titanium clip releaser 33 dismisses the clip 12.

Alternatively, the in vivo magnet 11 can be integrated into an assembly by the supporting set 15.

First Embodiment

Figure 7:
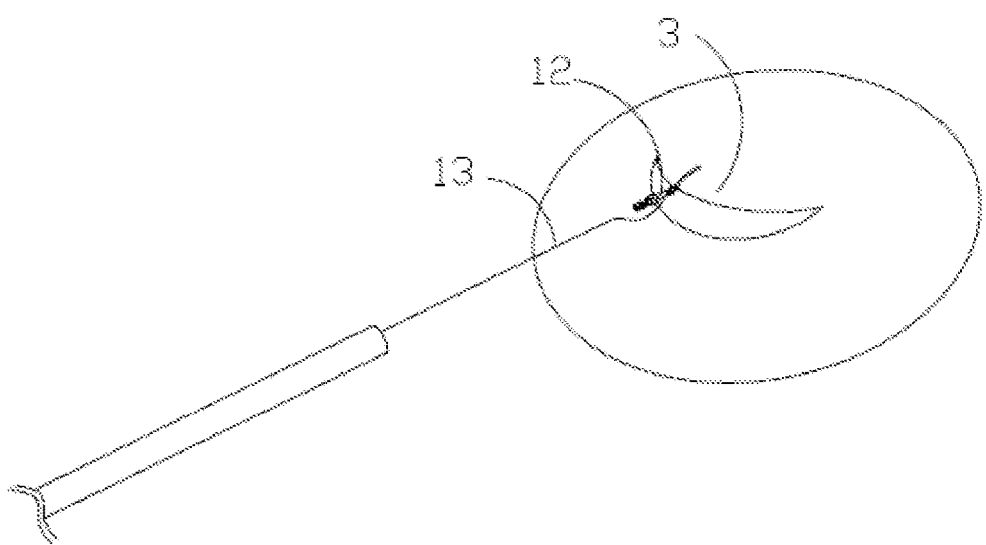
FIG. 7 depicts the delivery of a clip to body cavity in accordance with the first embodiment of the present disclosure.

FIG. 7 to FIG. 10 schematically illustrate the operation process of the present disclosed auxiliary apparatus, which is uniformly radially polarized. Referring to FIG. 7, when an end of the surgery target 3 on a mucous membrane is resected, the clip 12 and the connective thread are delivered to appropriate site on the resected mucous membrane by the cannula-assisted endoscope 31. The clip 12, join to an end of the connective thread, takes hold of the surgery target 3 and fixes it at the incision of the mucous membrane. After that, the titanium clip releaser 33 separates the clip 12 from the cannula-assisted endoscope 31. FIG. 7 schematically illustrates the situation after the clip 12 is dismissed from the cannula-assisted endoscope 31.

Figure 8:
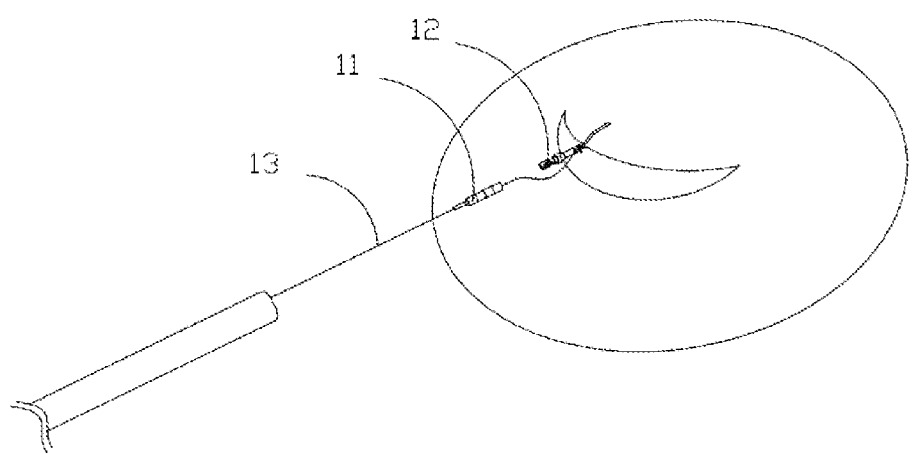
FIG. 8 depicts the delivery of an in vivo magnet to body cavity based on FIG. 7.

FIG. 8 schematically illustrates the in vivo magnet 11 and the holding set 14 being introduced into the body cavity. Assisted by the guiding wire 32, the cannula-assisted endoscope 31 sequentially disposes the in vivo magnet 11, which is constructed of three magnetic cylinders having hollow column-shaped centers, and a soft plastic tube on the connective thread, and positions them via the connective thread to the side of the first clip 12. In this process, the connective thread is parallel with the incision of the surgery target 3. Three magnetic cylinders having hollow column-shaped centers are uniformly radially polarized as depicted in FIG. 4.

Figure 9:
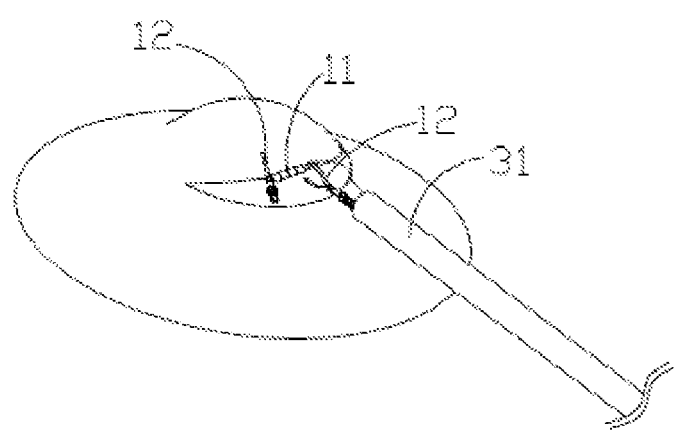
FIG. 9 depicts the delivery of another clip to body cavity based on FIG. 8.

After inserting the in vivo magnet 11 and the soft plastic tubes into body cavity, as depicted in FIG. 9, the cannula-assisted endoscope 31 delivers the second clip 12 near to the soft plastic tubes. The second clip 12 takes hold of the soft plastic tubes and anchors at the resected mucous membrane. Herein, the length direction of the in vivo magnet 11 is parallel with the incision. After that, the titanium clip releaser 33 dismisses the clip 12 from the cannula-assisted endoscope 31.

Figure 10:
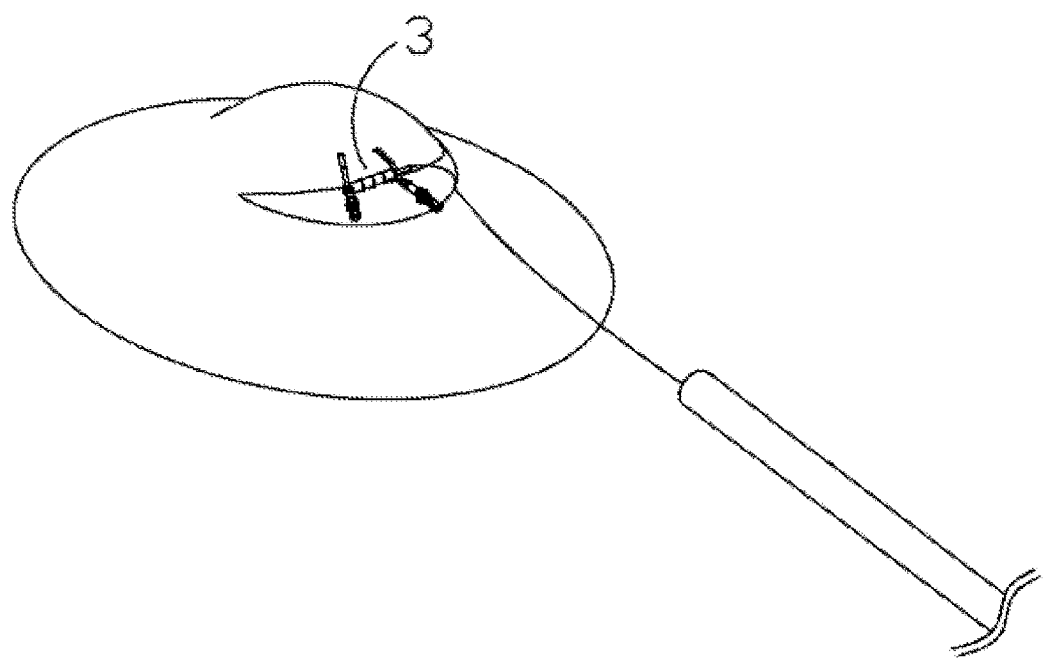
FIG. 10 depicts the anchoring of an in vivo device to a surgery target based on FIG. 9.

Finally, as depicted in FIG. 10, the connective thread at the distal end of the plastic tube that is distant from the in vivo magnet 11, is cut off to integrate two clips 12, the in vivo magnet 11 and the soft plastic tube into a unit which anchors to the recision of the surgery target 3 via two clips 12. The cannula-assisted endoscope 31 moves far away from the in vivo magnet 11 to perform further operation.

Two clips 12 and the in vivo magnet 11 are integrated via the connective thread. When the spherical magnet 21 of the in vitro device 2 moves and rotates outside the body, as depicted in FIG. 1, the in vivo magnet 11 driven by the magnetic force may control two clips 12 to manipulate the surgery targets 3 on the anchored mucous membrane to activate accordingly. Typically, the spherical magnet 21 controls clips 12 and the in vivo magnet 11 to overcome gravity. Thereby the visualization of surgical field is clarified and the surgery can be performed smoothly.

Alternatively, the in vivo magnet 11 can be held by the supporting set 15 before it is delivered to the body cavity. Two clips are respectively disposed at the external sides of the bed 1511 and the top cover 152. More specifically, uncovering the base 151 and the top cover 152, surrounding the supporting column 1512 with the magnetic cylinders having hollow column-shaped centers, and engaging the top cover 152 to the supporting column 1512 results in the integration of the in vivo magnet 11 by the supporting set 15. And then the connective thread passes through the hole 153 to introduce the in vivo magnet 11. In this process, a plurality of magnetic cylinders having hollow column-shaped centers is held by the base 151 and the top cover 152 to prevent them from falling apart.

Second Embodiment

Figure 11:
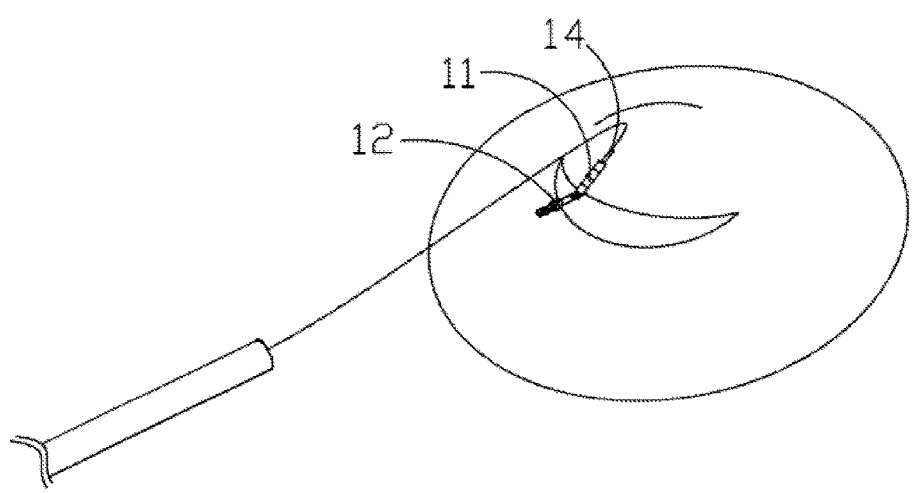
FIG. 11 depicts the delivery of a clip to body cavity in accordance with the second embodiment of the present disclosure.
Figure 12:
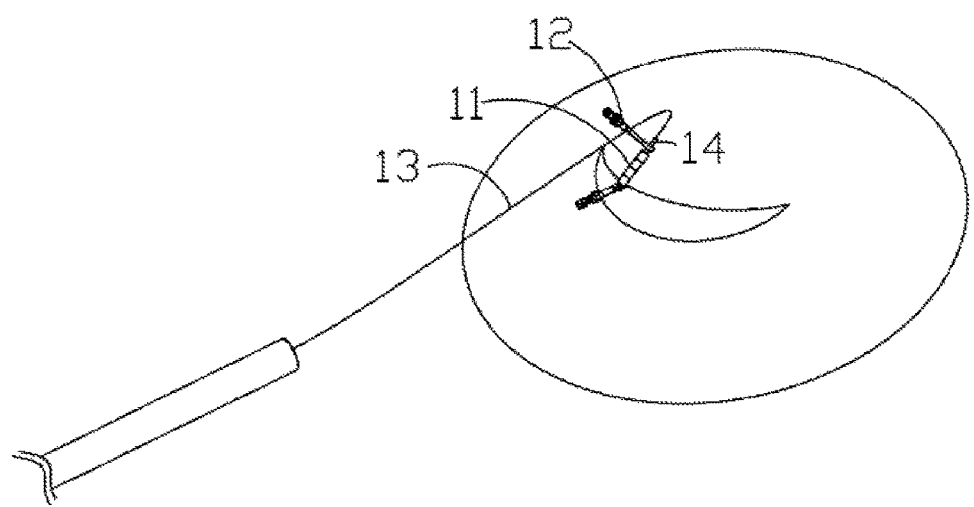
FIG. 12 depicts the anchoring of an in vivo device to a surgery target based on FIG. 11.

FIG. 11 to FIG. 12 schematically illustrate the operation process of the present disclosed auxiliary apparatus, which is uniformly longitudinally polarized. As depicted in FIG. 10, after the surgery target 3 is resected, the clip 12 and the connective thread are delivered to the appropriate site on the resected mucous membrane by the cannula-assisted endoscope 31. The clip 12, joined to one end of the connective thread, anchors to the incision of mucous membrane, and then is released from the cannula-assisted endoscope 31.

After that, as illustrated in the first embodiment, the in vivo magnet 11 and the holding set 14 are delivered into the body cavity. With the assistance of the guiding wire 32, the cannula-assisted endoscope 31 sequentially threads the in vivo magnet 11, which is constructed of four magnetic cylinders having hollow column-shaped centers, and a silicone tube on the connective thread, and then positions them to one side of the first clip 12 via the connective thread. In this process, the connective thread is perpendicular to the incision of the surgery target 3. Four magnetic cylinders having hollow column-shaped centers are uniformly longitudinally polarized as depicted in FIG. 5.

As depicted in FIG. 12, the cannula-assisted endoscope 31 positions the second clip 12 near to the silicone tube. The second clip 12 takes hold of the tube, and anchors to the surgery targets 3 on the mucous membrane with appropriate spacing to the incision, and then is dismissed from the cannula-assisted endoscope 31.

Figure 13:
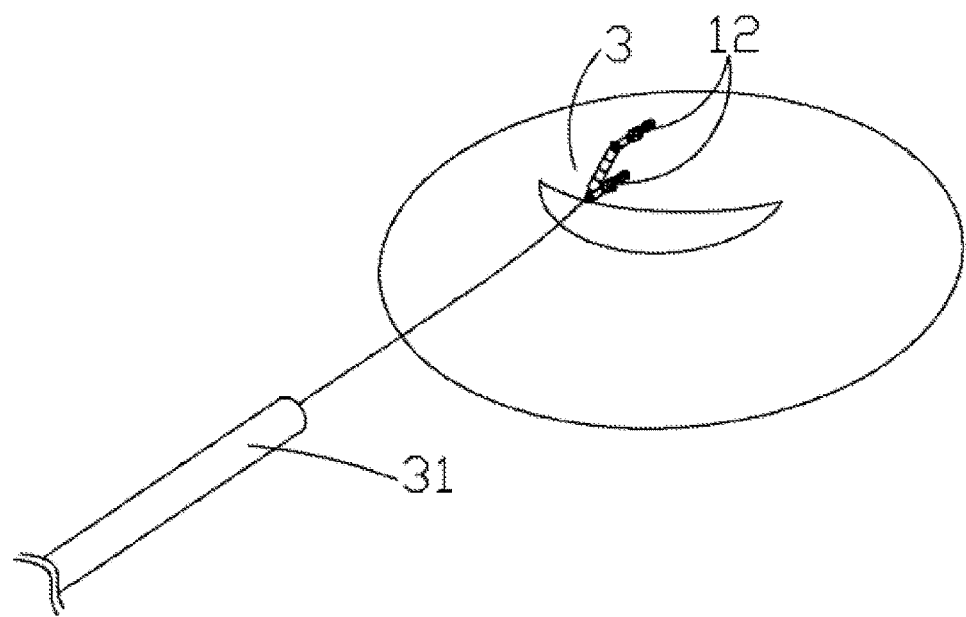
FIG. 13 depicts the anchoring of an in vivo device to a surgery target with a connective thread being cut off.

Finally, as depicted in FIG. 13, the connective thread at the distal end of the plastic tube that is distant form the in vivo magnet 11, is cut off to make two clips 12, the in vivo magnet 11 and the silicone tube to be integrated into an assembly which is anchored to the surgery target 3 through two clips 12. And then the cannula-assisted endoscope 31 moves far away from the in vivo magnet 11 to perform further operation.

Alternatively, the first clip 12 may anchor to the surgery targets 3 on the mucous membrane with appropriate spacing to the incision. And then the in vivo magnet 11 and the tube are delivered near to the first clip 12, and the second clip 12 is positioned at the incision. Meanwhile, the in vivo magnet 11, before being delivered into body cavity, can by held into an assembly via the supporting set 15. The operation is similar in manner with the first embodiment and will not be described here.

Two clips 12 and the in vivo magnet 11 are integrated into a unit through the connective thread. When the spherical magnet 21 of the in vitro device 2 moves outside the body, as depicted in FIG. 3, the in vivo magnet 11, driven by the magnetic force, may manipulate two clips 12 to control the anchored surgery targets 3 on the mucous membrane to activate accordingly. When the in vitro magnet 21 rotates, the in vivo magnet 11 rotates together to bend the surgery target 3, resulting in wrapping of the surgery target 3 on the surface of the in vivo magnet 11. Thereby, visualization of the surgical field is expanded.

In the above embodiments, the connector 13 joints the in vivo magnet 11 and the clip 12, and guides their delivery.

The present disclosure makes the surgery target 3 on the resected mucous membrane overcome gravity by controlling the in vivo magnet 11 via the in vitro magnetic field in ESD, resulting in the exposure of the visual field for the dissection and the improvement of the resection efficiency.

Figure 14:
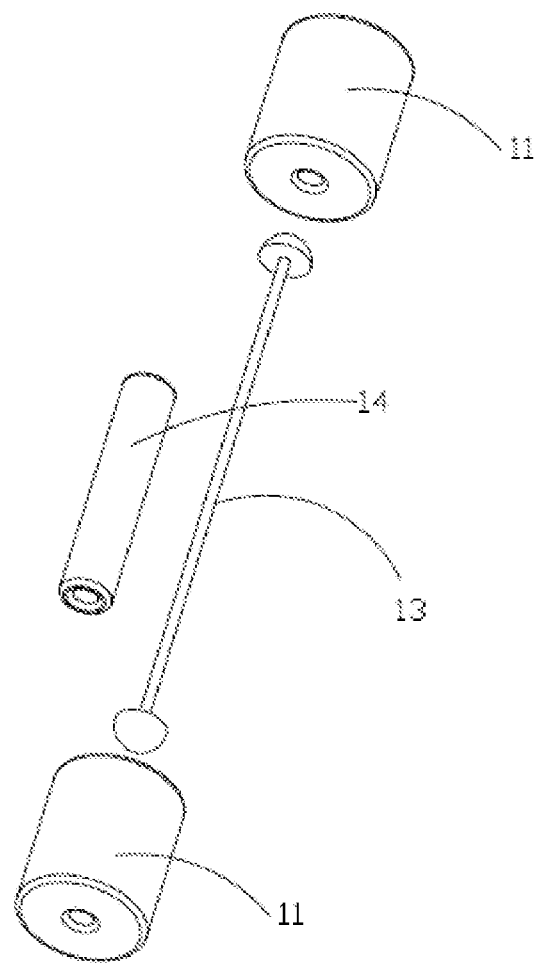
FIG. 14 depicts an in vivo device in accordance with the second embodiment.

In the second embodiment, as depicted in FIG. 14, it is different from the first embodiment in that the in vivo device 1 includes two sets of in vivo magnets 11 which are spaced apart and jointed by the connector 13. The clip 12, which is positioned between two sets of the in vivo magnets 11, is also linked to the connector 13. Herein, the connector 13 is stiff to allow two sets of in vivo magnets 11 to conquer the magnetic power and thereby be set apart. Moreover, the holding set 14, comprised of soft plastic or silicone tube, houses a portion of the connector 13 between two sets of in vivo magnets 11. Thereby, two sets of in vivo magnets 11, stiff connector 13, and the holding set 14 are joined to a magnetic composition via stiff connector 13 in use. Meanwhile, the clip 12 takes hold of the holding set 14 and the surgery target 3 so as to anchor the in vivo device 1 to the surgery target 3.

For like poles repel, same poles of the two sets of in vivo magnets 11 oppositely face in case that the opposite poles attract each other. Integrated by stiff connector 13 may prevent one of the two sets of in vivo magnets 11 from rolling-over by the magnetic force of attraction for each other.

Each set of the in vivo magnets 11 may comprise one or more magnetic cylinders.

In this embodiment, each set of in vivo magnet 11 may couple with a supporting set 15 respectively, or, two sets of in vivo magnet 11 share a supporting set 15. Herein, stiff connector 13 is pipe-shape to enclose the supporting column 1512.

Third Embodiment

Figure 15:
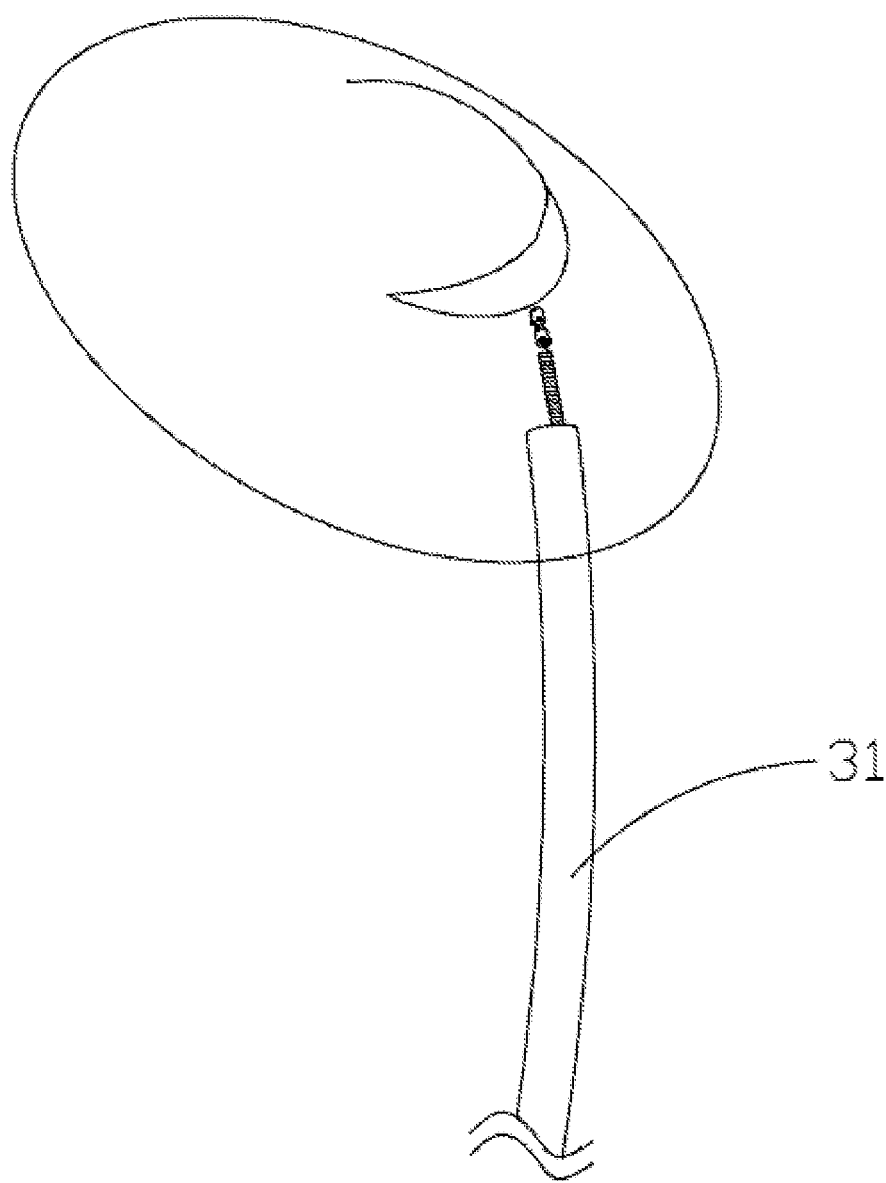
FIG. 15 depicts a set of magnet delivered to body cavity.
Figure 16:
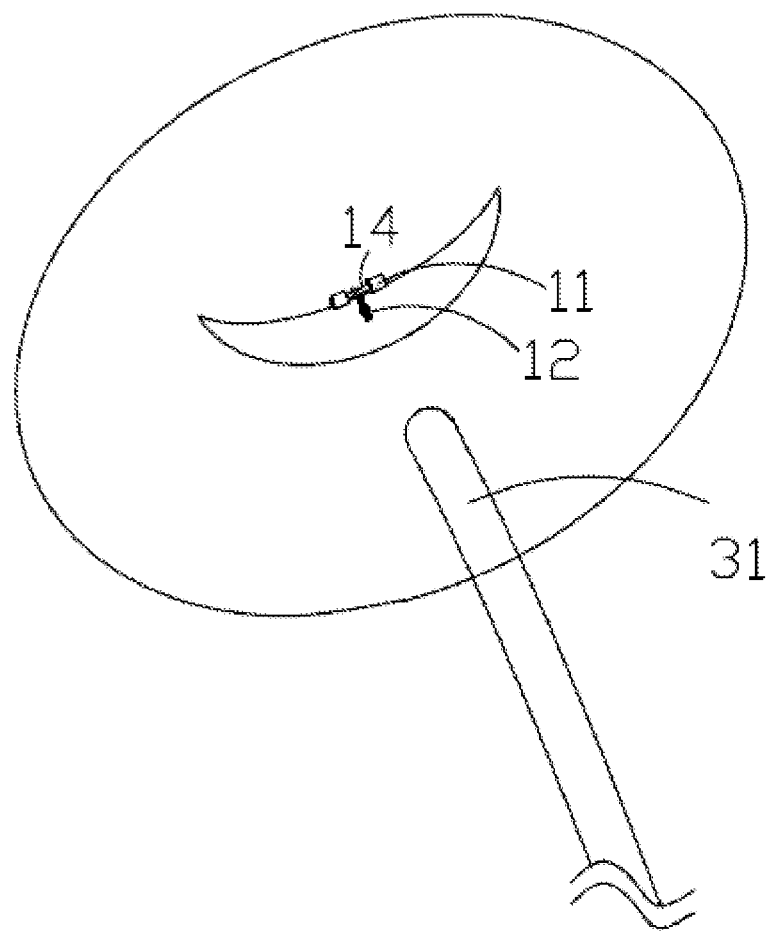
FIG. 16 depicts the anchoring of an in vivo device to a surgery target via a clip.

As depicted in FIG. 15 and FIG. 16, the first knot is tied at one end of the stiff connector 13. Then the stiff connector 13 sequentially passes through the first set of the in vivo magnet 11, the holding set 14 and the second set of the in vivo magnet 11. The second knot is tied at the other end of the stiff connector 13, close to the second set of the in vivo magnet 11. the sizes of the first and second knots match with the internal diameter of the in vivo magnets 11 to assemble two sets of the in vivo magnets 11 and the holding set 14 into an assembly.

In an embodiment, each set of the in vivo magnet 11 may couple with a supporting set 15 to form individual assembly. Alternatively, the stiff connector may be set in shape of cylinder, which can sequentially assist the first set of the in vivo magnets 11, the holding set 14 and the second set of the in vivo magnet 11 to house the supporting column 1512. In this instance, only one supporting set 15 is needed.

After the surgery target 3 is resected, the cannula-assisted endoscope 31 delivers sets of the in vivo magnet 11, which is threaded to the soft connective thread, to the incision on the mucous membrane. The cannula-assisted endoscope 31 positions the clip 12 to the incision via the soft connective thread and adjusts the delivered items to appropriate sites. And then the clip 12 is released to take hold of the holding set 14 and the incision of surgery target 3. The connective thread is cut off at the distal end of the second knot that is far away from the in vivo magnet 11 to integrate the clip 12 and the in vivo magnets 11 into an assembly being anchored to the surgery target 3 via the clip 12. Finally, the spherical magnet 21 drives the in vivo magnet 11 to manipulate the in vivo device 1, resulting in the resected surgery target 3 to overcome gravity and expose the visual field for dissection.

In this embodiment, the connector 13 is different from the soft connective thread, which guides and delivers the in vivo magnet 11 and the clip 12.

Figure 17:
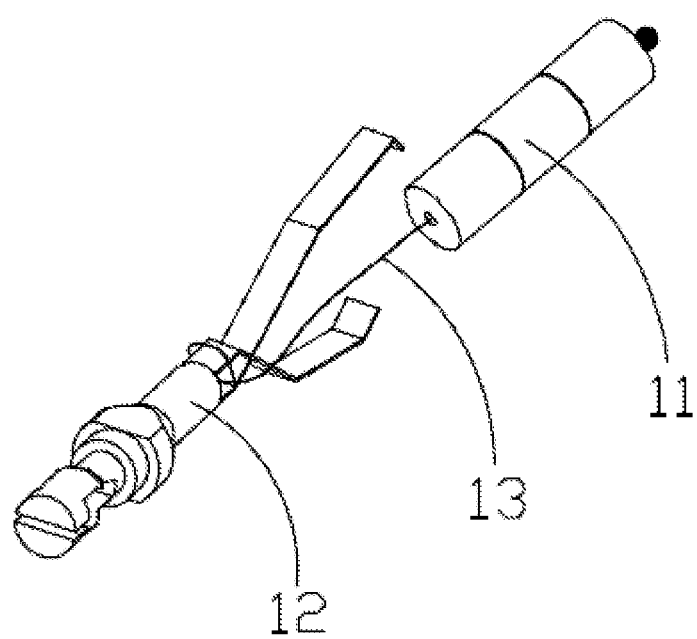
FIG. 17 depicts an in vivo device in accordance with the third embodiment.
Figure 18:
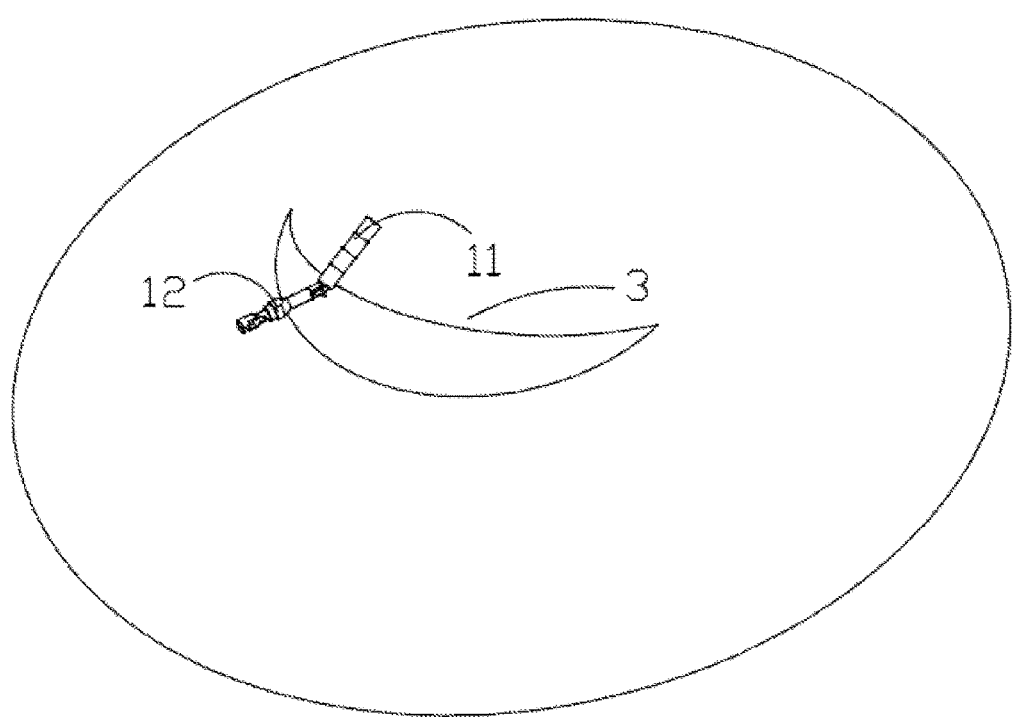
FIG. 18 depicts the anchoring of an in vivo device, as illustrated in FIG. 17, to a surgery target.

FIG. 17 and FIG. 18 schematically illustrate the third embodiment, which is different from the first embodiment in that the in vivo device 1 includes the clip 12, which anchors the in vivo device 1 to the surgery target 3. The clip 12 connects to side of the in vivo magnet 11. When the supporting set 15 is applied, the clip 12 disposes on the surface of the bed 1511 or the top cover 152. In this embodiment, the connector 13 is soft connective thread. A knot is tied at one end of the soft connector. The other end passes through the in vivo magnet 11 and then forms a loop by tying a scaffold, midshipman's hitch or slipknot. The loop, which may encircle the clip 12 includes a drawing member which is a portion of the thread forming the loop. The drawing member is used to adjust the diameter of the loop. The loop is collapsed by pulling the drawing member to joint the clip 12 to the connector 13, resulting in the assembly of the in vivo magnet 11 and the clip 12.

After the surgery target 3 is resected, the cannula-assisted endoscope 31, the guide wire 32 and the titanium clip releaser 33 deliver the in vivo magnet 11 and the clip 12 near to the incision and then release the clip 12 to grip the edge of the incision.

In the process, the in vivo magnet 11 and the clip 12 form an assembly via the soft connective thread. As depicted in FIG. 3, when the spherical magnet 21 of the in vitro device 2 moves and rotates, the in vivo magnet 11, driven by the magnetic force, activates accordingly to manipulate the clip 12. If the surgery target 3 is small in size, the in vitro magnet 21 moves to drive the in vivo magnet 11 and correspondingly control the clip 12 to grasp and retract the surgery target 3 to increase the visualization of surgery. If the surgery target 3 is large, besides the above method, the in vitro magnet 21 may rotate to drive the in vivo magnet 11 and accordingly make the surgery target 3 wrapped at the surface of the in vivo magnet 11 to gradually expand the visual field.

Figure 19:
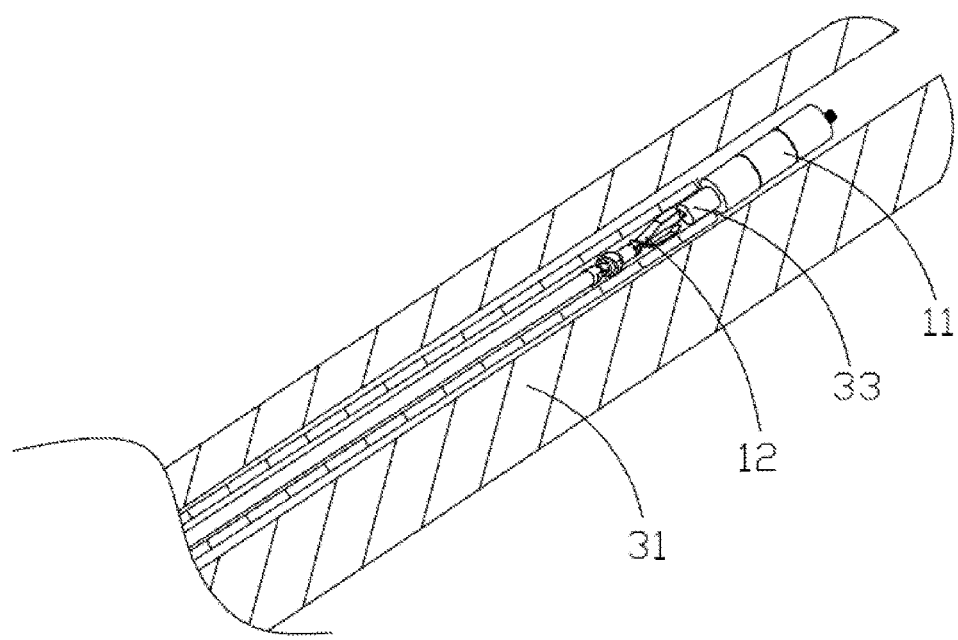
FIG. 19 depicts an in vivo device received by a cannula-assisted endoscopy in accordance with the forth embodiment.
Figure 20:
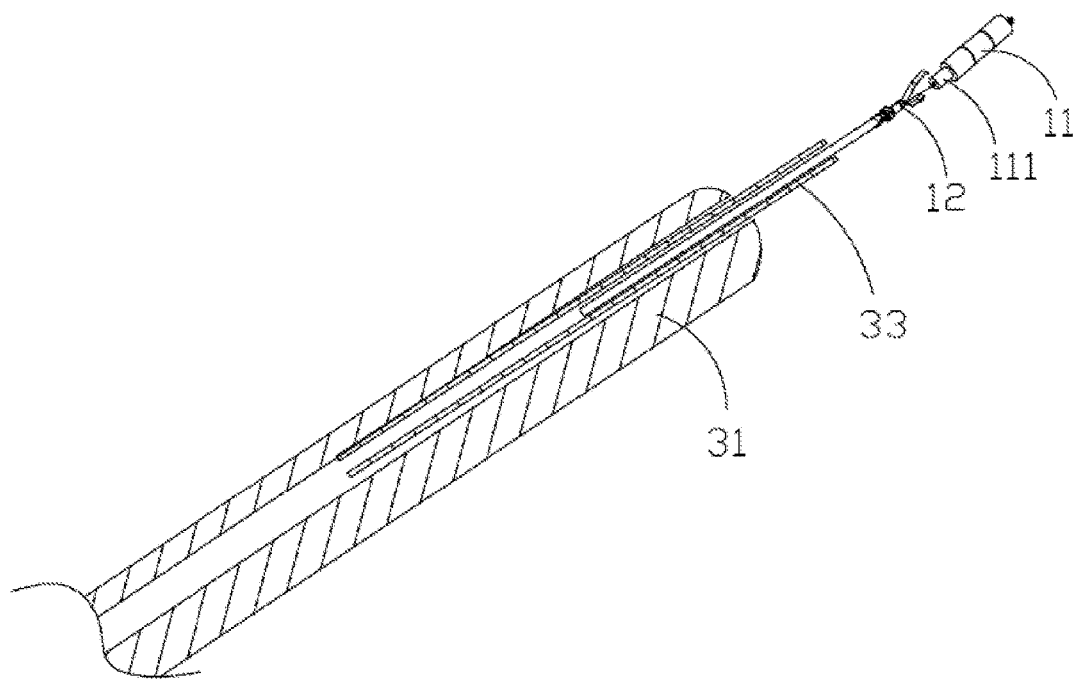
FIG. 20 depicts the delivery of an in vivo device, as illustrated in FIG. 17, to body cavity.
Figure 21:
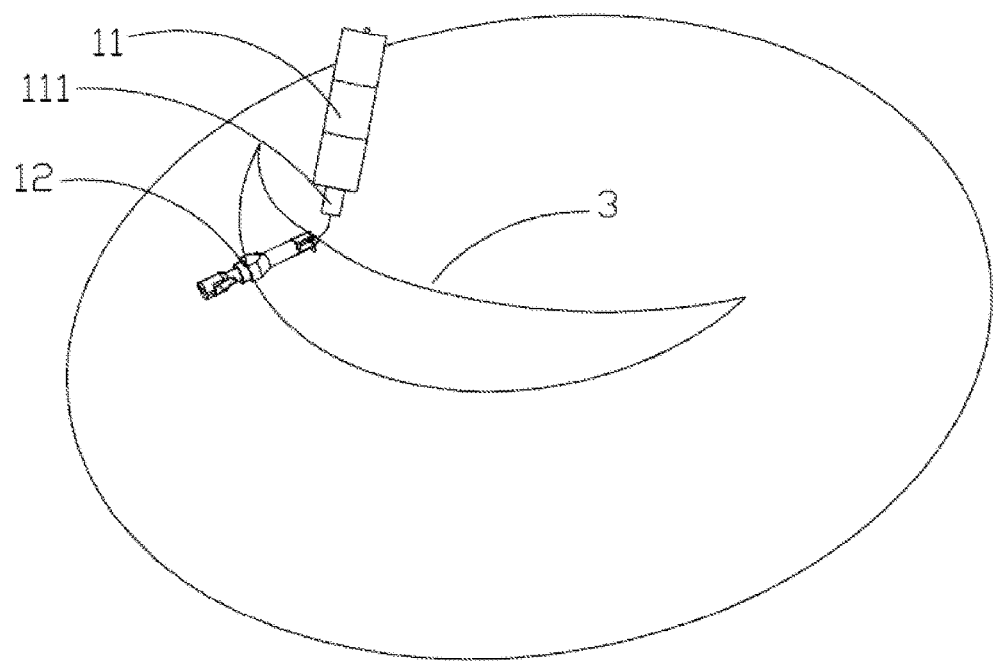
FIG. 21 depicts the anchoring of an in vivo device to a surgery target in accordance with the fourth embodiment.

In the forth embodiment, as depicted in FIG. 19 to FIG. 21, the in vivo magnet 11 comprises a guide mean 111 at the side close to the clip 12. Referring to FIG. 19, the diameter of the guide mean 111 matches with the internal diameter of the titanium clip releaser 33. Therefore, it is convenient to harbor the in vivo magnet 11 to the titanium clip releaser 33 for delivery.

Figure 22:
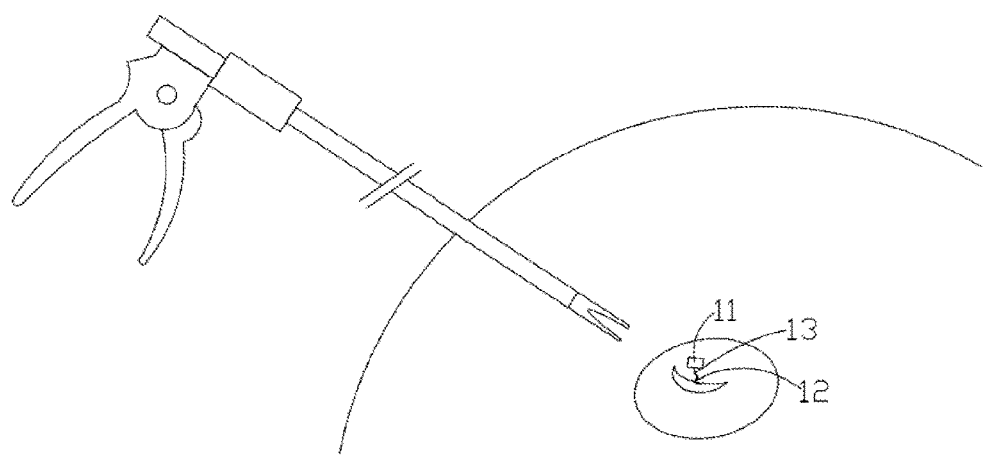
FIG. 22 depicts the anchoring of an in vivo device to a surgery target in accordance with the fifth embodiment.

In the fifth embodiment, as depicted in FIG. 22, it is different from the third embodiment in that the volume of the in vivo magnet 11 is bigger and the clip 12 is in shape of hook. The in vivo magnet 11 consists of one or two magnetic cylinders having hollow column-shaped centers, which are connected to each other side by side. The length of the magnetic cylinder is from 2 mm to 20 mm with the external diameter from 1.5 mm to 10 mm and the internal diameter from 0.3 mm to 2.4 mm.

The in vivo magnet 11, illustrated in this embodiment, is applicable for laparotomy, which punctures a channel on the abdominal cavity and delivers the in vivo device 1 to the surgery target 3 via the channel with the assistance of auxiliary tools.

In summary, the present disclosure anchors the clip 12 to the surgery target 3 and manipulates the in vivo device 1 through the in vitro magnetic field generating device to make the resected surgery target 3 overcome gravity to expose the visual field of surgery. Moreover, the method to control the disclosed auxiliary apparatus makes the surgery target 3 wrap the in vivo device 1 via the uniform magnetic field created by the in vitro magnetic field generating device to expand the visual field.

In the scope of the present invention, in one embodiment a target area is a target lesion area, which needs to be removed from the normal tissue. In one embodiment, the target lesion area is located in a target organ. In one example, the target organ is a hollow organ. In one example the target organ can be accessed through a working channel inserted from a natural opening into the hollow organ.

The present invention describes a method to use the minimal invasive system described herein for a surgery operation. The method includes introducing an in vivo magnet in close proximity to a target lesion area of the target organ, wherein the in vivo magnet has an in situ magnet moment; attaching the in vivo magnet to the target lesion area through an in vivo anchoring element; and providing an in vitro magnetic field-generating element, configured to move or and rotate the in vivo magnet according in three dimension corresponds to the direction change of the external magnetic field.

Figure 29:
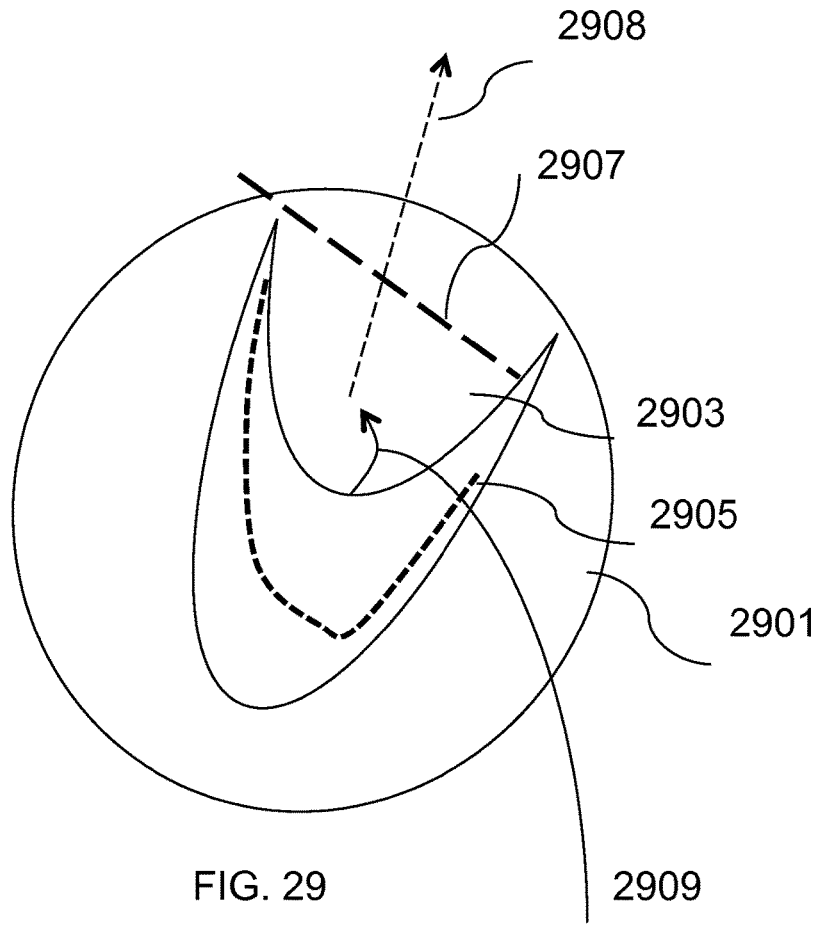
FIG. 29 illustrates a method to remove a target lesion area from a target organ.

The purpose for the surgery is to remove the target lesion area from the normal tissues of the target organ. Therefore the target lesion area is pulled continuously or progressively along a first direction to allow the target lesion area to be separated from the rest of the target organ. Almost concurrently, the target lesion area is cut off from the rest of the target organ and generating a cutting line. As the target lesion area being pulled forward and cutting lines evolves. In each pulling and cutting step, the cutting line and the first direction of movement of the target lesion area are not parallel to each other but form an angle. In one example, the angle is between 35-145 degrees. In another example, the angle is between 75-125 degrees. In another example, the angle is between 80-100 degrees. In one example, when the target lesion area is separated from a target organ, to external in vitro magnet is moved in order to move the target lesion area clockwise or counter clockwise to expose the cutting line or area of the target organ underneath. Referring to FIG. 29, elements in the FIG. 29 are the follows:

2901 target organ
2903 target lesion area to be removed
2905 a previous position of the target lesion area
2907 cutting line
2908 overall progressive movement direction of the target lesion area
2909 rolling up of the separated portion of the target lesion area As shown, the target lesion area is moved from a previous position 2905 to a current position 2903. 2908 indicates the overall progress direction of the target lesion area that has separated and the cutting line 2907 is almost perpendicular to the movement direction 2908.

In one embodiment of the method disclosed herein, the in vivo anchoring element only connects with the target lesion area in one predetermined position throughout the surgery, because the in vivo anchoring element further attached with a permanent magnetic body.

In one embodiment of the method disclosed herein, two in vivo anchoring elements are used to attach to the target lesion area. The method comprising using two in vivo anchoring elements to pull a target lesion area progressively along a first direction, comprising tying a first anchoring element using a first string; introducing the first anchoring element tied with the first string into a hollow organ having a lesion area, by using a working channel inserted from a natural opening into the hollow organ; attaching the first anchoring element in a first predetermined location of the lesion area; introducing at least one permanent magnetic body having a hollow center along the string into the hollow organ having a lesion area, by using the working channel inserted from the natural opening into the hollow organ; anchoring a second anchoring element in a second predetermined location of the lesion area; and rolling portions of the lesion area including a interface between a normal tissue area and the lesion area using a magnetic field-generating element arranged on the outside of the hollow organ so that the first and second anchoring elements are moved three dimensionally in response to the movement of the magnetic field-generating element. In order to avoid or minimize interfaces between the magnetic bodies closely attached to the two anchoring elements, the first and second anchoring element is at least 2 cm apart. In one example, the permanent magnetic body is arranged linearly between the first and second anchoring elements.

In another example, due to the size of the target lesion area, two anchoring elements are used but the two anchoring elements are positioned less than 2 cm and the second anchoring elements attached to the first string.

In the scope of the present invention, a uniform magnetic field means the absolute value of magnetic field gradient is less than 1-4 Gauss/mm. In one example, the absolute value of magnetic field gradient is less than 4 Gauss/mm. In another example, the absolute value of magnetic field gradient is less than 3 Gauss/mm. In another example, the absolute value of magnetic field gradient is less than 2 Gauss/mm. In another example, the absolute value of magnetic field gradient is less than 1 Gauss/mm.

It is to be understood, however, that even though numerous characteristics and advantages of preferred and exemplary embodiments have been set out in the foregoing description, together with details of the structures and functions of the embodiments, the disclosure is illustrative only; and that changes may be made in detail within the principles of the present disclosure to the full extent indicated by the broadest general meaning of the terms in which the appended claims are expressed.

What is claimed is:

1. A method for using an auxiliary apparatus for MIS (minimally invasive surgery) comprising
   a) using an in vitro magnetic field generating element to provide an external magnetic field interacting with an in vivo magnet;
   b) changing a direction of the external magnetic field to manipulate the in vivo magnet which in turn makes a surgery target wrap the in vivo magnet under a uniform magnetic field after an incision on the surgery target occurred.

2. The method according to claim 1, wherein the in vitro magnetic field generating element provides a uniform magnetic field.

3. The method according to claim 1, wherein the in vivo magnet comprises one or more permanent magnetic bodies connected side by side, each having a hollow center and are configured to be uniformly radially or longitudinally polarized.

\* \* \* \* \*